United States Patent [19]

Amos et al.

[11] 4,210,026
[45] Jul. 1, 1980

[54] BLOOD SAMPLE COLLECTING MEANS

[75] Inventors: Lynn G. Amos, Painted Post; Charles M. Beechey, Pine City; Charles H. Rogers, Corning, all of N.Y.

[73] Assignee: Corning Glass Works, Corning, N.Y.

[21] Appl. No.: 386

[22] Filed: Dec. 29, 1978

[51] Int. Cl.² .............................................. B01L 3/02
[52] U.S. Cl. .................................................. 73/425.6
[58] Field of Search ............... 73/425.6; 128/760, 763, 128/765, 767; 222/103; 141/25, 26

[56] References Cited

U.S. PATENT DOCUMENTS

| | | | |
|---|---|---|---|
| 2,574,797 | 11/1951 | Nelson et al. | 222/103 |
| 3,297,558 | 1/1967 | Hillquist | 141/25 |
| 3,450,309 | 9/1969 | Millo | 222/103 |

*Primary Examiner*—S. Clement Swisher
*Attorney, Agent, or Firm*—Walter S. Zebrowski; William J. Simmons, Jr.; Richard E. Kurtz

[57] ABSTRACT

A hand-held device for causing a blood sample to be controllably drawn into a flexible envelope or the like. The envelope is placed between a rigid and a hinged member disposed within the housing of the device, and a roller advanced along the hinged member to progressively compress the envelope. When the wheel is moved back along its path, the envelope is allowed to progressively expand thereby drawing the blood sample into the envelope.

12 Claims, 5 Drawing Figures

BLOOD SAMPLE COLLECTING MEANS

BACKGROUND OF THE INVENTION

The present invention relates to blood collection apparatus, and more particularly to a suction-type of apparatus for filling a flexible envelope.

Various means are known for drawing up blood samples, and generally fall into two categories. In a first category is the syringe-type of collection apparatus wherein a vein is punctured and a sample withdrawn through a hollow needle. With such an apparatus, samples of relatively large volumes may be taken. The second category of collection means comprises capillary tubes. As their name implies, such tubes are of very small diameter and depend upon capillary action to cause blood to be drawn into the tubes. Such tubes are commonly used to obtain small blood samples, taken from a skin wound made by a pin prick or the like. As is well known, the skin wound technique is preferred in many situations. For instance, frequently with elderly people veins are prone to collapse and the use of a syringe is undesirable. Also, for taking blood samples from infants a skin wound technique is preferred to the use of a syringe since veins are quite small and hard to locate.

Due to the necessarily small diameter of the capillary tubes, their volume is extremely limited. For many procedures it is desirable that a sample comprise at least 200 microliters of blood. This requires the use of a number of capillary tubes; and further, the discharge of samples from many small tubes involves an undesirable amount of re-handling of the blood samples.

An improved, easily controllable pipetter well adapted for the drawing of blood samples is disclosed in co-pending application Ser. No. 876,340, filed Feb. 9, 1978 and entitled "Hand-Held Pipetter". With such a device a flexible reservoir is coupled to a rigid, elongate tube and a roller progressively collapses and then re-distends the reservoir to cause fluid to be drawn into the tube. The fluid is subsequently discharged from the tube into another vessel for treatment, analysis or the like. In order that air be expelled and subsequently drawn into the reservoir both ends thereof are open, and secured in the apparatus housing by means of adapters or the like.

In most cases it has been necessary to discharge the sample from capillary tubes, fillable reservoirs, and the like into another vessel for treatment and/or analysis. In some cases attempts have been made to treat a sample while in a capillary tube; with one approach a tiny ferromagnetic element is disposed within the capillary tube and agitated by placing a magnet adjacent the tube and moving it back and forth. In general such efforts have not been completely successful, and moreover the cost of such devices is relatively high. On the other hand, when the sample must be discharged into another container for treatment valuable time is lost and damage to sample material can occur.

Accordingly, it will be seen that it would be highly desirable to provide a blood sample collection means which serves to fill a detachable reservoir whose volume is considerably greater than that of a capillary tube, and which is adapted for initiating treatment of a blood sample.

Another object of the invention is to provide a blood sample collection device for filling a flexible sample-transporting envelope.

Yet another object is to provide means for drawing a blood sample into a flexible envelope bearing a sample treating agent.

Still another object of the present invention is to provide a blood sample collection apparatus having substantially greater volume than a capillary tube and adapted for drawing blood from a skin wound.

SUMMARY OF THE INVENTION

Briefly stated, in accordance with one aspect of the invention the foregoing objects are achieved by providing an elongate housing adapted to be gripped in the hand of a user and bearing a support surface and a movable, hinged member adjacent thereto. A compression wheel is disposed in the housing and constrained by a track or the like to move generally parallel to the support surface, bearing upon the hinged member and urging it toward the support surface. A resilient envelope is disposed between the hinged member and the support surface and, as the compression wheel urges the hinged member toward the support surface the envelope is progressively flattened, purging it of air. When the compression wheel is caused to retreat, the resiliency of the envelope urges the hinged member upwardly and the expanding envelope draws the sample therein. When the compression wheel has fully retreated the open end of the envelope can be sealed and the sample transported to an appropriate site for treatment or analysis.

In one embodiment of the invention the interior surface of the envelope is treated with an agent for treating the sample immediately as it enters the envelope.

BRIEF DESCRIPTION OF THE DRAWING

While the specification concludes with claims particularly pointing out and distinctly claiming the subject which is regarded as the invention, it is believed that the invention will be better understood from the following description of a preferred embodiment taken in conjunction with the accompanying drawings in which:

DESCRIPTION OF THE PREFERRED EMBODIMENT

Figure 1:
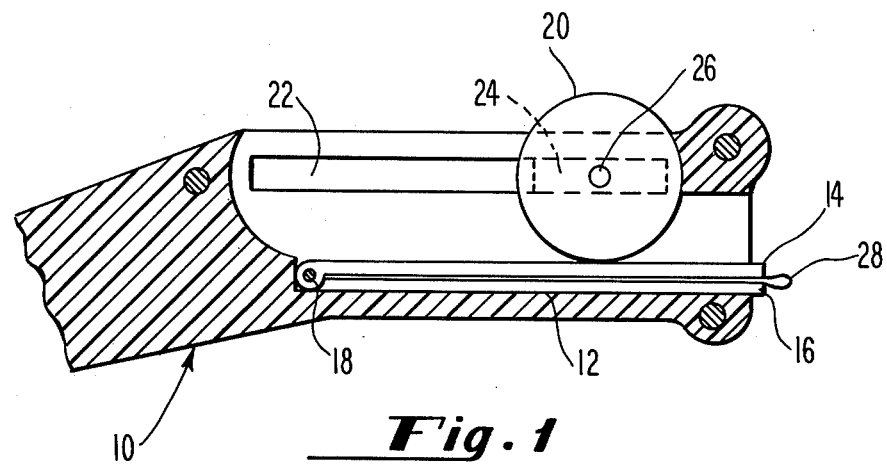
FIG. 1 is a sectioned elevational view of a collection device formed in accordance with the invention.

The sample collector shown in FIG. 1 comprises an elongate housing generally indicated at 10 which includes a handle portion (sectioned in the Figure, more fully visible in FIG. 3) and a forward, envelope-bearing section. The latter portion of the housing comprises a generally flat, elongate support surface 12 which bears a pinching means including a hinged member 14. In the embodiment illustrated, the hinged member 14 is coupled to a rigid lower member 16 by a pin 18 or the like. A compression wheel 20 is disposed above the pinching means, and more particularly directly above the upper surface of hinged member 14. The compression wheel is slidably located within the housing 10, being retained in an elongate slot 22 by means of a slider 24 into which a pivotal axle 26 of the wheel is received.

It will be understood that the sectional portion of the housing, not visible in the Figure, is substantially the same as the visible portion and includes a slot or track which complements track 22, and which receives another slider supporting the near side of axle 26 of compression wheel 20.

Disposed within the pinching means is a resilient tubular envelope 28, which in a preferred embodiment comprises a tube formed of polyvinyl chloride, silicone rubber, or other resilient material having a non-thrombogenic surface. The material should also be inert in the presence of a blood sample, so as not to change the characteristics of the sample. The tube should be sufficiently resilient so that, after being completely flattened and purged of air as shown in FIG. 1, it will expand to its original dismensions when pressure is released therefrom.

The pinching means generally comprises upper and lower member 14 and 16, respectively, and may be formed of any suitable rigid material such as metal or plastic. Further, while in a presently-preferred embodiment the pinching means is slidably received in housing 10 for engagement by compression wheel 20, and may thereby be easily withdrawn and re-loaded into the housing at will, it will be appreciated that the hinged member 14 may alternatively be pivotally fixed within the housing 10 and cooperate with a support surface which is an integral part of the housing. In this manner the function of lower member 16 would be fulfilled by a surface formed in the material of the housing itself.

Compression wheel 20 is advantageously formed of a material which exhibits a high coefficient of friction against hinged member 14 thereby to afford enough traction to cause the wheel to roll along the upper surface of the hinged member as it is urged forwardly by manual pressure. A suitable compression wheel may be easily formed from a resilient material such as rubber or the like; or may be constructed of an inner member of rigid plastic, metal or the like and a peripheral "tire" of a resilient material which provides the necessary traction to allow wheel 20 to be rolled along the hinged member 14. The specific materials used for the members, and the particular manner in which the various members are formed, may be varied to suit individual applications and it is anticipated that such variations in detail are within the contemplation of those skilled in the art.

Figure 2:
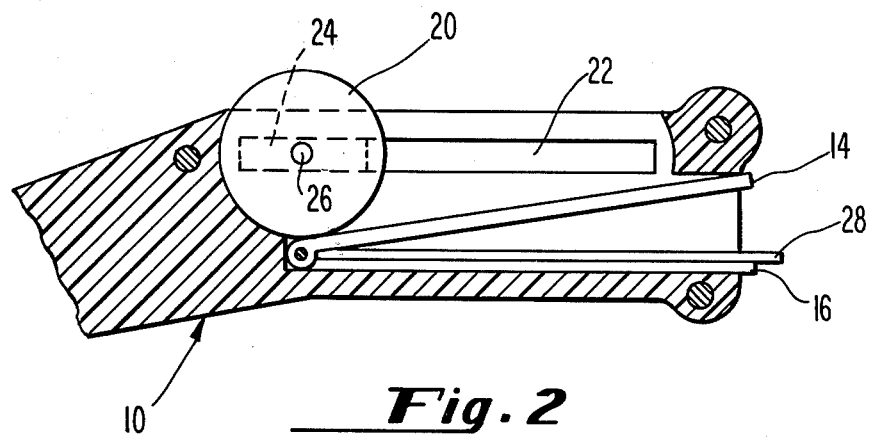
FIG. 2 is a sectioned view as in FIG. 1 with the apparatus in an "open" position.

FIG. 2 illustrates the inventive apparatus in an open or "loaded" condition. Compression wheel 20 has been manually urged to its extreme rearward position, having rolled rearwardly along the upper surface of hinged member 14 and along guideway 22. As the compression wheel moves rearwardly, the resilient nature of envelope 28 urges hinge member 14 upwardly. In this manner as the internal volume of the envelope expands, a less-than-atmospheric pressure is produced at its entrance so that liquid may be drawn into the envelope. The amount of liquid drawn into the envelope, and the rate at which it is drawn, is controlled by the positioning of compression wheel 20 and the speed with which it is rolled rearwardly. When the wheel reaches its rearwardmost position, as shown in FIG. 2, substantially all pressure is released from the pinching means and envelope 28 may be removed. Alternatively the pinching means, including lower member 16 and the hinged upper member 14, may be manually withdrawn from the housing and the envelope 28 subsequently removed therefrom.

Figure 2A:
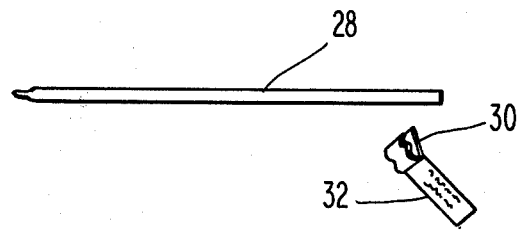
FIG. 2a is a view of an envelope for use with the apparatus of FIGS. 1 and 2.

Referring now to FIG. 2a, envelope 28 is illustrated along with a clip 30 having a tag 32 attached to it. The leftward end of envelope 28 is closed by means of heat sealing or the like, so that the tube comprises an elongate envelope having a single opening at its rightward end. When the tube is placed between hinged element 14 and an underlying, rigid support surface the resiliency of the tube supports the hinged member and the tube remains substantially in an uncompressed condition. As the hinged member is urged downwardly against the underlying supporting surface by means of the translation of compression wheel 20, envelope 28 is progressively flattened commencing with the leftward or closed end and continuing until substantially the entire envelope is flattened. It will now be understood that this flattening of the tube serves to purge substantially all of the air from within the interior of the tube, preparing it for the introduction of a blood sample.

As the pressure upon the hinged member is gradually released, as by leftward translation of compression wheel 20, the hinged member is allowed to retreat from the underlying support surface, being urged upwardly by the resiliency of envelope 28. The envelope progressively expands to substantially its original size, and in so doing draws in the blood sample in which the open end of the envelope is immersed.

When envelope 28 has expanded over substantially its entire length, and is therefore filled with the sample, the open end of the envelope is pinched closed by the application of clamp 30. The identity of the sample is indicated upon tab 32 and the sample-bearing envelope may be dispatched immediately for treatment and/or analysis. It will be evident that it is not necessary for a sample to completely fill the envelope; the withdrawal of a sample may be stopped at any point merely by ceasing to rotate the compression wheel. At this point the open end of the envelope may be clamped closed and the envelope dispatched for treatment or analysis. Since the envelope was purged preparatory to receiving the sample, it is unlikely to contain any air and therefore the premature drying or clotting of a blood sample will not occur.

In a preferred embodiment of the present invention the interior surface of the envelope may be coated with an agent for treating a blood sample. In many instances it is desirable to treat a newly-drawn blood sample with an anti-coagulant such as EDTA, Heparin or sodium citrate. In other cases, it is desired to add a coagulant to the sample to accelerate the clotting time. In still other instances it may be desirable to add fluoride to the sample to preserve the glucose content. In all of the foregoing examples, and in many others, it is anticipated that the treating agent may be coated directly upon the inner surfaces of the envelope for treating the sample immediately after it is drawn. This provides the advantage of immediate contact between the sample and the treating agent without any intervening delay. Moreover, since the envelope is of a flexible, resilient nature the treating agent may be readily mixed therewith by flexing or kneading the envelope.

It is envisioned that a sample may be drawn into a pre-treated envelope, the envelope closed, and treatment of the sample begun immediately so that by the time a sample reaches a laboratory or other analysis facility sample treatment is practically complete and analysis may commence immediately.

It will now be appreciated that rather than relying upon capillary action, the present invention makes use of atmospheric pressure for introducing a sample into the sample-bearing envelope. Accordingly, the diameter of the envelope is not limited to the minute size necessary to sustain capillary action; and the volume of the envelope may be substantially greater than that of ordinary capillary tubes. Accordingly, with the present invention much larger samples may be collected in a single envelope, rather than in multiple capillary tubes.

Efforts have been made to introduce reactant materials into capillary tubes, and mix them with a sample therein. While it has been possible to introduce the reactant into the capillary tube, due to the extremely small diameter of the tube mixing has presented a difficult problem. With the present invention a much larger sample is present, and it is possible to flex and knead the envelope to achieve a thorough mixing of the materials.

Figure 3:
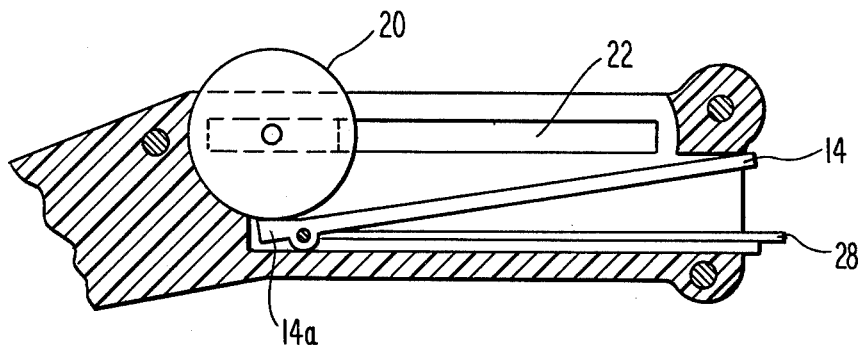
FIG. 3 illustrates another embodiment of the invention.

In FIG. 3 there is shown another embodiment of the invention in which a rearward extension 14a has been added to hinged member 14. By providing a ramp-like surface upon extension 14a as compression wheel 20 retreats it levers the hinged member 14 upwards, thereby positively causing pinching means 14 to release envelope 28.

Figure 4:
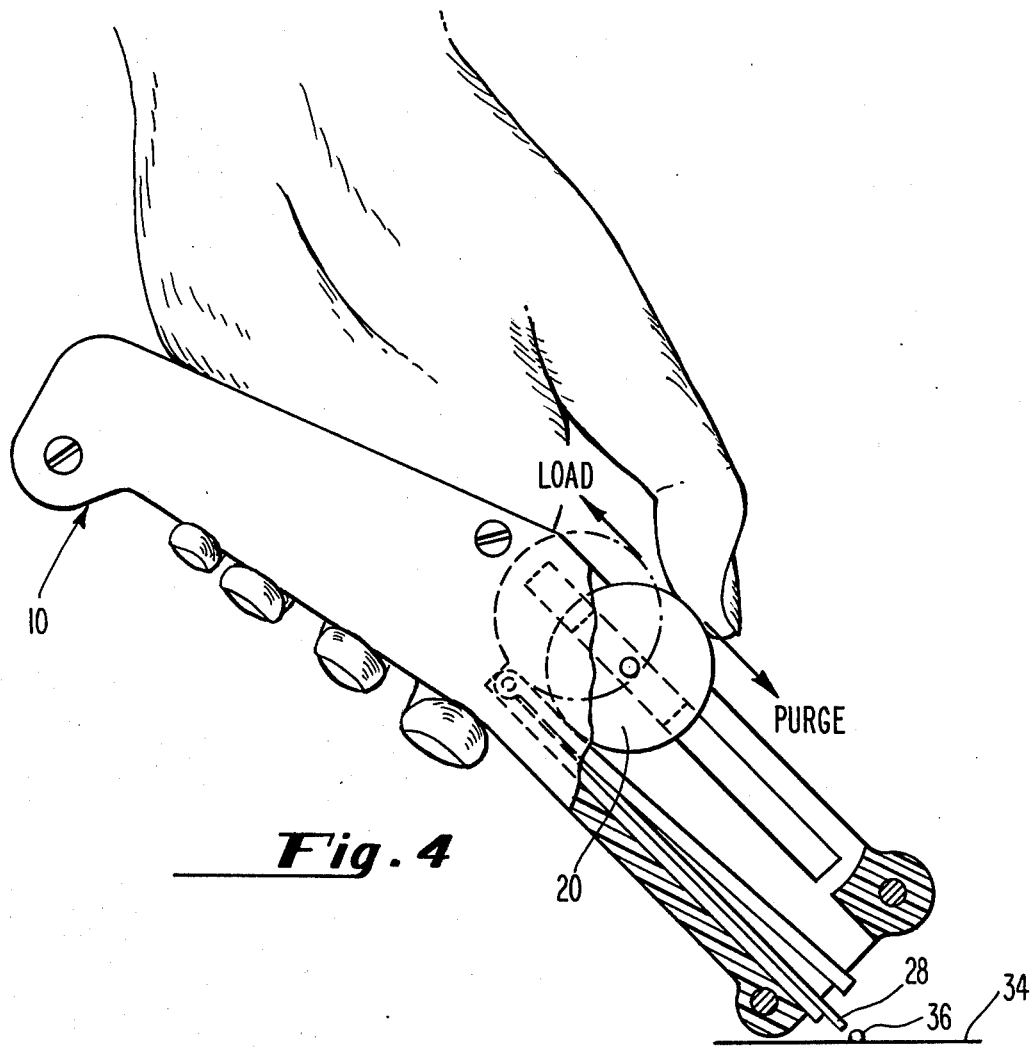
FIG. 4 illustrates the manner of using the inventive apparatus.

FIG. 4 illustrates the overall configuration of a sample collecting means formed according to a presently preferred embodiment, and illustrates the manner of use. The housing 10 is gripped in one hand as shown, and the thumb used to urge compression wheel 20 forward to purge the sample envelope 28. A wound is then made in the skin surface 34, and a drop of blood 36 caused to well up in the usual fashion. The distal end of envelope 28 is then brought into contact with the drop of blood, and the thumb used to roll compression wheel 20 rearwardly, causing a sample to be drawn into the envelope. The apparatus is then withdrawn from wound site and a clamp applied to the distal end of the envelope. The hinged pinching means may then be removed from the housing, carrying the envelope therewith; or the envelope itself may be withdrawn from the pinching means and transported to a laboratory or the like for analysis.

It ill now be understood that there has been disclosed herein an improved blood collection apparatus which allows the facile collection of substantially larger samples than are ordinarily collectible through the use of capillary tubes, and further allows the immediate reaction and mixing of a sample with a reactant material.

As will be evident from the foregoing description, certain aspects of the invention are not limited to the particular details of the examples illustrated, and it is contemplated that other modifications or applications will occur to those skilled in the art. For example, depending upon the specific configuration of the sample-receiving envelope and the surface upon which it rests, the guide means defining the path of the compression wheel or slider may deviate from a straight line in order to provide a desired purging and/or drawing characteristic. It is accordingly intended that the appended claims shall cover all such modifications and applications as do not depart from the true spirit and scope of the application.

What is claimed is:

1. Means for collecting a blood sample for subsequent treatment or analysis, comprising:
   a housing adapted to be gripped in the hand of a user and defining a support surface therein;
   pinching means hingedly disposed within said housing and extending generally parallel to said support surface;
   a resilient envelope removably disposed between said pinching means and said support surface; and
   a rotatable wheel movably retained within said housing adjacent said pinching means and manually translatable along said pinching means for advancing said pinching means toward said support surface thereby compressing said resilient envelope and for retreating along said pinching means whereby said envelope is decompressed.

2. Means according to claim 1 further including a blood-treating material disposed upon the interior surface of said envelope.

3. Means according to claim 2, wherein said material is an anti-coagulant.

4. Means according to claim 2 wherein said material is of a type which accelerates clotting.

5. Means according to claim 1 further including retaining means cooperating with said housing and said compression means for constraining said compression means to follow a predetermined path.

6. Means according to claim 2 wherein said envelope is formed of lined medical-grade polyvinyl chloride tubing.

7. Means according to claim 1 wherein said compression means comprises a rotatable wheel.

8. An improved hand-held means for collecting a volume of blood comprising:
   housing means adapted to be gripped in the hand of a user;
   a compression wheel disposed in said housing means;
   said housing means defining a path along which said compression wheel may be translated;
   an elongated support surface disposed within said housing means;
   pinching means hingedly disposed within said housing means intermediate said compression wheel and said support surface;
   a resilient tubular envelope having a first, closed end and a second, open end and disposed between said pinching means and said support surface, said first end of said envelope being proximate the hinged point of said pinching means;
   whereby translation of said compression wheel along said pinching means in one direction urges said pinching means toward said support surface thereby effecting progressive compression of said envelope, and translation of said compression wheel in the opposite direction allows said pinching means to retreat from said support surface thereby allowing progressive expansion of said envelope to cause blood to be drawn therein.

9. Means according to claim 8, further including a blood-treating material disposed within said envelope.

10. Means according to claim 8, wherein said compression wheel is formed of a resilient material which effects good traction upon said pinching means.

11. Means according to claim 8, wherein said elongate support surface and said pinching means are formed by a pair of elongate members pivotally coupled at one end thereof.

12. Means according to claim 8, wherein said pinching means comprises a first portion on one side of a pivot point and overlying said envelope, and a second portion at the opposite side of said pivot point, and wherein the path of said compression wheel extends past said pivot point to allow said compression wheel to bear upon said second portion of said pinching means for positively causing said pinching means to release said envelope.

* * * * *